US010545124B2

United States Patent
Ozbal

(10) Patent No.: US 10,545,124 B2
(45) Date of Patent: Jan. 28, 2020

(54) AUTOMATED SAMPLE FRACTIONATION PRIOR TO MASS SPECTROMETRIC ANALYSIS

(71) Applicant: PureHoney Technologies, Inc., Billerica, MA (US)

(72) Inventor: Can Ozbal, Lexington, MA (US)

(73) Assignee: PureHoney Technologies, Inc., Lexington, MA (US)

(*) Notice: Subject to any disclaimer, the term of this patent is extended or adjusted under 35 U.S.C. 154(b) by 0 days.

(21) Appl. No.: 16/159,309

(22) Filed: Oct. 12, 2018

(65) Prior Publication Data

US 2019/0265211 A1 Aug. 29, 2019

Related U.S. Application Data

(63) Continuation of application No. 15/392,546, filed on Dec. 28, 2016, now Pat. No. 10,101,307, which is a continuation of application No. 14/750,693, filed on Jun. 25, 2015, now Pat. No. 9,557,317.

(60) Provisional application No. 62/017,170, filed on Jun. 25, 2014.

(51) Int. Cl.
| *G01N 30/72* | (2006.01) |
| *G01N 33/49* | (2006.01) |
| *G01N 30/60* | (2006.01) |
| *G01N 30/08* | (2006.01) |

(52) U.S. Cl.
CPC ......... *G01N 30/7233* (2013.01); *G01N 30/08* (2013.01); *G01N 30/6091* (2013.01); *G01N 30/6095* (2013.01); *G01N 33/491* (2013.01)

(58) Field of Classification Search
CPC ............... G01N 30/7233; G01N 30/08; G01N 30/6091; G01N 30/6095; G01N 33/491
See application file for complete search history.

(56) References Cited

U.S. PATENT DOCUMENTS

| 5,601,991 | A  | 2/1997  | Oberhardt |
| 5,612,178 | A  | 3/1997  | Gordon et al. |
| 5,866,004 | A  | 2/1999  | Houck et al. |
| 8,502,985 | B2 | 8/2013  | Weinberger et al. |
| 8,759,753 | B1 | 6/2014  | Di Bussolo et al. |
| 9,252,003 | B2 | 2/2016  | Hermanson et al. |
| 9,768,001 | B2 | 9/2017  | Cooper |
| 2004/0142488 | A1 | 7/2004 | Gierde et al. |
| 2007/0263046 | A1 | 11/2007 | Iwasa et al. |
| 2008/0213906 | A1 | 9/2008 | Aurand et al. |
| 2010/0291588 | A1 | 11/2010 | McDevitt et al. |

(Continued)

OTHER PUBLICATIONS

Davison, "Potential problems with using deuterated internal standards for liquid chromatography tandem mass spectrometry," Ann Clin Biochem. 2013. p. 1.

(Continued)

*Primary Examiner* — Dennis White
(74) *Attorney, Agent, or Firm* — Mintz Levin Cohn Ferris Glovsky and Popeo, P.C.

(57) ABSTRACT

Systems, apparatus, methods, and kits are provided for automated mass spectrometric analysis of small volumes of liquid samples, such as biological samples. The systems, apparatus, and kits may be used in facilities where high throughput of samples, as well as reliable and repeatable assay results with little training of staff, are needed. Such facilities include hospital emergency wards.

17 Claims, 7 Drawing Sheets

400A TOP VIEW OF CARTRIDGE

410 Solvent inlet ports with tapered fittings
215 Sample + internal standard introduction port
450 Notched corner acts as a key to prevent insertion into device in an incorrect orientation
Wash Solvent
Elution Solvent
460 Outlet port to MS 215
405
445 Bar code assures correct cartridge is loaded in the device
455 Uniquely shaped port to prevent solvent errors
425 Solvent mixing chamber
220 Filter
240 Immobilized chromatography media

400B SIDE VIEW OF CARTRIDGE

410 Solvent inlets
215 Sample+ internal standard introduction port
460 Outlet port: waste or MS
405
220 Filter
425 Solvent mixing chamber
430 Filtrate reservoir
240 Immobilized chromatography media

(56) References Cited

U.S. PATENT DOCUMENTS

2012/0037724 A1    2/2012  Prentice et al.
2012/0176627 A1    7/2012  Weinberger et al.
2013/0206653 A1*   8/2013  Brann .................... G01N 30/30
                                                           210/85

OTHER PUBLICATIONS

Dwivedi, "Characterization of *Arabidopsis thaliana* mutant ror-1 (roscovitine-resistant) and its utilization in understanding the role of cytokinin N-glucosylation pathway in plants," Plant Growth Regul. (2010) 61:231-242.
International Search Report for Application No. PCT/US2015/037698, dated Sep. 30, 2015. (3 Pages).

* cited by examiner

AUTOMATED SAMPLE FRACTIONATION PRIOR TO MASS SPECTROMETRIC ANALYSIS

CROSS REFERENCE TO RELATED APPLICATIONS SECTION

This application is a continuation of U.S. application Ser. No. 15/392,546, filed Dec. 28, 2016, which is a continuation of U.S. application Ser. No. 14/750,693, filed Jun. 25, 2015, now U.S. Pat. No. 9,557,317, which claims the benefit of priority to U.S. Provisional Patent Application No. 62/017,170, filed Jun. 25, 2014, entitled "AUTOMATED SAMPLE FRACTIONATION PRIOR TO MASS SPECTROMETRIC ANALYSIS," the contents of which are hereby incorporated by reference in their entirety.

FIELD

The subject matter described herein relates to systems, apparatus, methods, and kits related to mass spectrometric analysis of liquid samples of small volume, such as mass spectrometric analysis of bodily fluids in a clinical setting.

BACKGROUND

Detection of specific chemical species in liquid solutions can be a complicated task in which an array of analytical equipment is used. In some instances, utilizing a marker, such as luminescent or radioactive markers which identify the target species, or analyte, can lack precision or sensitivity in some cases. Increasingly, mass spectrometry (MS) with an atmospheric pressure ionization (API) source is used by those seeking to quantify one or more analyte in a complex liquid solution. Mass spectrometric analysis requires that the sample be ionized, that is to say that the species in the sample have a mass and a net charge, either positive or negative. The atmospheric pressure ionization source converts charge-neutral analytes into ions in the gas phase that can be analyzed with mass spectrometry.

An atmospheric pressure ionization source can achieve ionization of species in a liquid sample in various ways. Some of the most common techniques are electrospray ionization (ESI) and atmospheric pressure chemical ionization (APCI). These two techniques have in common atomizing the sample by expelling the sample liquid through a narrow tube while heating the tube. Droplets of the sample liquid evaporate into the constituents of the sample, including the target chemical species. As the evaporated constituents of the sample travel from the narrow tube towards the mass spectrometer inlet, they travel through a large electrical potential and become ionized.

Mass spectrometric analysis is useful in quantifying medications or toxins in biological samples like blood, urine, or tissue extracts, as well as monitoring pesticides or pollutants in food or water. These types of sample solutions may contain high concentrations of salts or buffers, such as pH buffers, and these buffers make the ionization of analytes using electrospray ionization (ESI) or atmospheric pressure chemical ionization (APCI) highly inefficient. This effect is known as ion suppression and is the direct result of excess of salt becoming ionized instead of the analytes of interest. Currently, analysts using mass spectrometry (MS) fractionate complex samples prior to MS analysis, effectively separating out much of the analytes of interest from the salts or buffers prior to ionization. Fractionation is typically done by liquid chromatography (LC), most often high-pressure liquid chromatography (HPLC). Analysts use various chromatography media, solvents, additives and temperature to optimize the fractionation of analytes from interferents, such as salts and buffers. The direct coupling of high-pressure liquid chromatography (HPLC) fractionation to mass spectrometric (MS) analysis is very common and is known as high-pressure liquid chromatography-mass spectrometry (HPLC-MS).

Commercial systems for high-pressure liquid chromatography mass spectrometry (HPLC-MS) can be large, complicated systems. Such systems can include high-pressure liquid pumps, two or more solvent reservoirs, a solvent mixer to create the needed gradients in the solvent ratio, a valve or other sample introduction mechanism, a chromatography column for performing the fractionation, and a detector, which in the case of HPLC-MS is a mass spectrometry detector. The complexity of commercial HPLC-MS systems can vary and such systems may have the ability to perform at different pressures, may include automated sample introduction, may include temperature controls, and may include additional optical detectors, for example those capable of measuring light absorbance, fluorescence, or light scattering from a liquid sample.

When using a commercial high-pressure liquid chromatography-mass spectrometry (HPLC-MS) system, the user should have some degree of skill or knowledge to obtain accurate and reliable results. The user optimizes each analysis through multiple decisions, such as by selecting the correct chromatography media and solvents, though other variables can be controlled, such as temperature, pressure, sample size, and detection instrument parameters. Optimization depends not only on the nature of the sample, but also on the target species, or analyte. Detection of an analyte in blood can be very different from detecting the same analyte in urine in that the optimal conditions for high-pressure liquid chromatography (HPLC) fractionation may not be the same. The chromatography media that a skilled user selects may change according to the contents of the sample, and the solvents the skilled user selects need to be compatible with the ionization process for mass spectrometric analysis.

Commercial high-pressure liquid chromatography-mass spectrometry (HPLC-MS) systems may include two solvents (though one solvent of varying concentration can be used), a wash solvent and an elution solvent, being prepared for each analysis or batch of analysis. A skilled user prepares the solvents in concentrations appropriate for the sample and the selected chromatography media. It is typically the case that the ratio between the wash and elution solvents changes over time during fractionation, and in commercial systems, a skilled user may oversee this change in ratio between the solvents, which can also be thought of as a gradient in relative concentration in the solvents. The reason for this gradient, or change in ratio, in the solvents is that analytes and contaminants have differential affinity for the chromatography media as compared to the elution solvent. In most cases, analytes are preferentially bound onto the chromatography media in the presence of wash solvent, but as the relative amount of elution solvent is increased, the analyte will eventually become unbound from the chromatography media and flow out of the system with the elution solvent. The skilled high-pressure liquid chromatography-mass spectrometry (HPLC-MS) user understands the chemical properties of the analytes in each sample and selects appropriate high-pressure liquid chromatography (HPLC) conditions, including the wash and elution solvents and their relative concentration during fractionation, to obtain sufficient distinction between the contaminants in a sample and the desired analytes so that each can be detected.

The chromatographic columns used in commercial high-pressure liquid chromatography (HPLC) systems are quite large and designed for reuse. Since the media in the chromatographic columns are selected for different types of fractionation, multiple columns will often be associated with a commercial HPLC system. The size of the columns used in commercial HPLC systems can require a large amount of sample, as well as a large volume of solvents. Additionally, the intended long life-time of the chromatographic columns means that they are used multiple times, and so the skilled user, or analyst, needs to be cognizant of what the columns were used for in the past in order to determine the veracity of the results he or she obtains.

SUMMARY

Methods, systems, and apparatus, including computer program products, are provided for analysis of small volumes of liquid samples, such as biological samples, in systems using mass spectrometric analysis. The systems and apparatus include an analysis cartridge and a preloaded solvent assembly.

In some aspects, provided herein are systems for determining the concentration of an analyte of interest in a biological sample that includes a solvent assembly and a disposable cartridge. The solvent assembly may include a first volume of a first solvent and a second volume of a second solvent, the solvent assembly may further include a first outlet fluidly connected to the first volume and a second outlet fluidly connected to the second volume. The disposable cartridge can include a first solvent introduction port and a second solvent introduction port, a sample introduction port, a chromatography region, and an outlet fluidly connected to the chromatography region. The first solvent introduction port may be configured to accept the first outlet of the solvent assembly and to fluidly connect to the first volume, and the second solvent introduction port may be configured to accept the second outlet of the solvent assembly and to fluidly connect to the second volume. The sample introduction port may be fluidly connected to the first and second introduction ports. The chromatography region may be fluidly connected to the sample introduction port.

The following features may be present in systems for determining the concentration of an analyte of interest in a biological sample in any suitable combination. In some embodiments, the system may further include a sample analysis portion that is operably connected to the outlet of the disposable cartridge, in which the sample analysis portion can include a mass spectrometric analysis system, in which the mass spectrometric analysis system may produce a spectra for the analyte of interest, and may produce at least one of a plurality of isotopes of the analyte of interest or a plurality of derivatized samples of the analyte of interest added to the biological sample in a single spectral measurement. The system may further include at least one processor having operational thereon computer instructions for at least controlling operation of the system, to at least determine a concentration of the analyte contained in the biological sample and to report the at least one analyte concentration. In some embodiments, the system may include immobilized chromatography media in the chromatography region of the disposable cartridge. One or more filters in the disposable cartridge may be included in the system, in which the one or more filters may be configured to remove precipitates and/or insoluble material from the biological sample and yield a filtered biological sample. In some such embodiments, the system may include a filtrate reservoir in the disposable cartridge, in which the filtrate reservoir may have a metered volume and is configured to contain the filtered biological sample. The cartridge may include one or more internal standards, in which the one or more internal standards are provided in a dried form. The one or more internal standards may correspond to one or more predetermined assays. The immobilized chromatography media may correspond to one or more predetermined assays. The solvent assembly and the disposable cartridge may fit together in a specific orientation constrained by a key. In some embodiments, the key may include an asymmetrical first outlet, an asymmetrical second outlet, both asymmetrical first and second outlets, or an asymmetrical joining portion between the first and second outlets on the solvent assembly. In some systems, the disposable cartridge may include a receiver structure that complements the key and may be configured to allow the solvent assembly and the disposable cartridge to fit together in the specific orientation constrained by the key. The receiver structure can include at least one of the first solvent introduction port or the second solvent introduction port of the disposable cartridge. The first solvent and the second solvent of the solvent assembly may be compatible with the disposable cartridge to prepare the biological sample for an assay to determine the presence of the analyte of interest. The assay may include at least one of a metabolic acidosis assay, an intentional overdose assay, an uncontrolled convulsions or seizures assay, a coma assay, or a cardiovascular assay. In some embodiments, the assay may include one or more test panels. One or more codes indicating the compatibility of the solvent assembly with the disposable cartridge to perform the assay to determine the presence of the analyte of interest may be included in the system in some embodiments. The one or more codes may include color coding, written codes, machine readable codes, electrical signaling codes, or any combination thereof. In some such embodiments, the written codes may include alpha-numeric codes, symbols, or a combination of both. The machine readable codes may include symbols, quick response (QR) codes, barcodes, or any combination thereof. In some embodiments, the electrical signaling codes may include radio frequency (RF) signals. One or more correct insertion structures may be included on the disposable cartridge, in which the one or more correct insertion features may be configured to orient the disposable cartridge correctly within the system. The one or more correct insertion structures on the disposable cartridge may include a notched corner of the disposable cartridge. The first volume may be defined by a plunger assembly of a first syringe and the second volume may be defined by a plunger assembly of a second syringe. In some embodiments, a syringe pump configured to independently dispense the first solvent and the second solvent. The system may include a first seal located at the first outlet of the solvent assembly and a second seal located at the second outlet of the solvent assembly, in which the first seal and the second seal may prevent solvent from flowing out of the solvent assembly. A seal piercing mechanism on each of the first and second solvent introduction ports can be included in the system, in which each seal piercing mechanism is configured to break either the first seal or the second seal to allow solvent to flow into the disposable cartridge. A solvent mixing chamber may be included in the disposable cartridge, in which the solvent mixing chamber may be configured to at least receive the first and the second solvents from the solvent introduction port to form a mixed solvent, and may provide the mixed solvent to a reservoir that is fluidly connected to the sample introduction port.

The above-noted aspects and features may be implemented in systems, kits, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

Figure 1:
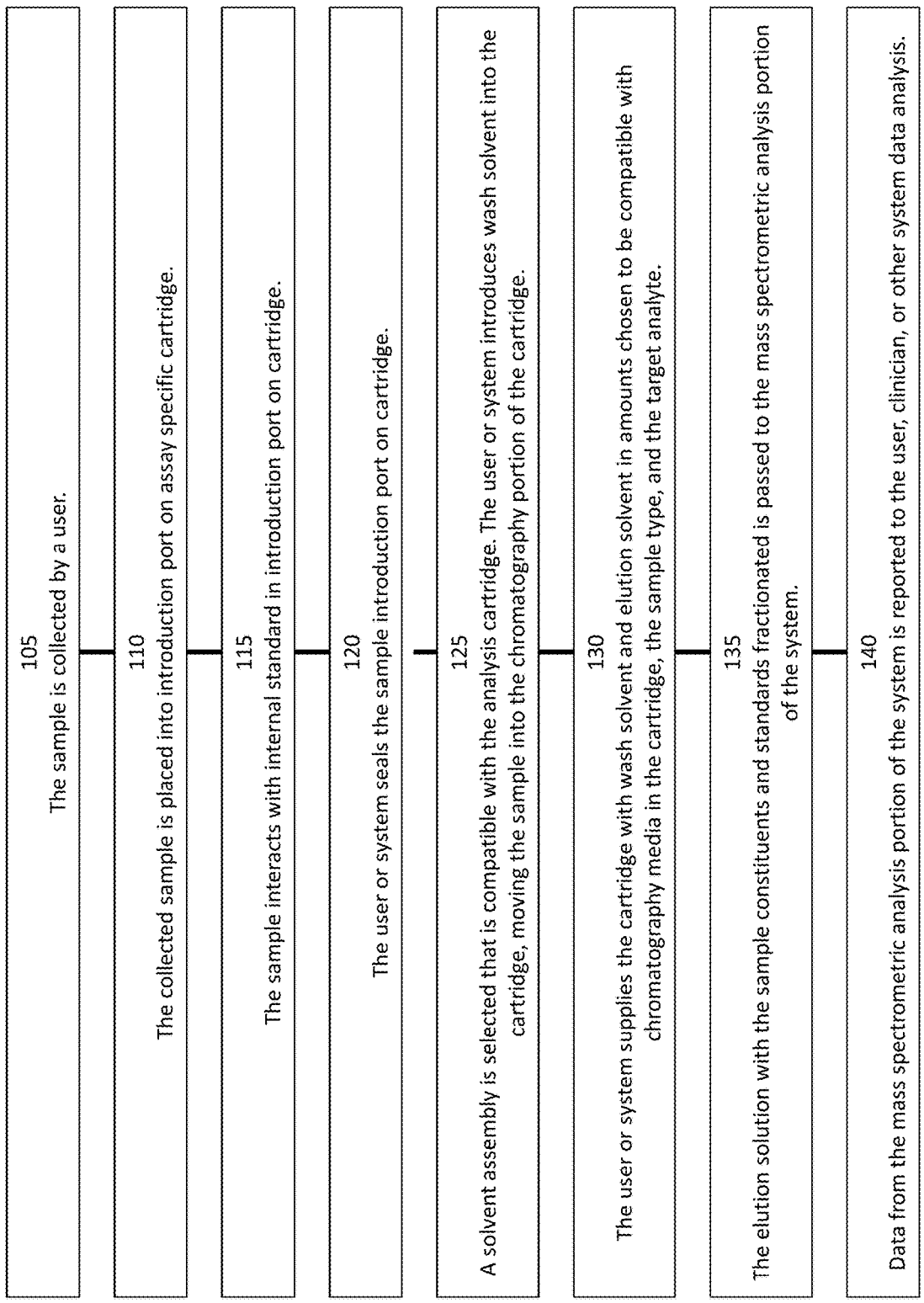
FIG. 1 depicts a flow diagram of solution movement within an exemplary analysis system that includes a mass spectrometer.

Like labels are used to refer to same or similar items in the drawings.

DETAILED DESCRIPTION

In some example embodiments, there is provided apparatus, systems, kits, and methods that provide single use chromatography materials for sample preparation for mass spectrometric (MS) analysis. Single-use, assay specific analysis cartridges which fractionate a biological sample for MS analysis, as described herein, may allow for the use of small sample size and may provide internal standards data analysis that can be used with single-use, disposable solvent-containing assembly. The single-use, assay specific cartridge in combination with the corresponding solvent assembly, may remove the need for users to be highly skilled in mixing solvents for chromatography; may allow for fewer errors, such as those due to reuse of fractionation media; may simplify the storage of solvents used in high-pressure liquid chromatography (HPLC); may reduce the amount of sample fluid needed; and/or may increase the speed and efficiency of obtaining high-pressure liquid chromatography-mass spectrometry (HPLC-MS) results.

The systems, which include single-use assay specific cartridges that have inlets for liquid samples, internal standards, fractionation media, and inlets for wash and elution solvents, as well as mass spectrometric analysis instrumentation, can be used as shown in FIG. 1. A sample, such as a biological sample, is collected, at 105, by a user. The biological sample may be blood, urine, or a homogenized tissue sample. The user may place, at 110, a small volume of the sample into a sample introduction port on the single-use cartridge. The sample inlet port may have one or more filters to remove items from the sample that would complicate fractionation and items that are not needed for determination of the presence of the target analyte. The one or more filters can remove items such as blood platelets and cells. Within, or adjacent to, the sample introduction port are one or more types of internal standards, that is to say chemical species that are present in a known amount and that should yield known results when an elution solution containing the standard is passed through a mass spectrometer. The internal standards may be provided in the single-use cartridge in a dried condition that is to say not in solution. After addition of the sample to the introduction port, the sample interacts, at 115, with the one or more internal standards to bring them into solution. The filtered sample and the internal standards are held in a filtrate reservoir beneath the sample introduction port and the one or more filters.

Once the sample is added to the introduction port on the single-use, assay specific cartridge, the user or the system seals, at 120, the sample introduction port that sits above the filtrate reservoir. This means that any fluid that enters the filtrate reservoir from fluid connections cannot exit through the sample introduction port. In some instances, one-way valves, such as check valves or flap valves, may guide the flow of fluid through the filtrate reservoir, so that fluid flows towards the chromatography portion of the single-use cartridge.

Without in any way affecting the scope of the claims, an advantage of some embodiments described herein is that a single-use solvent assembly and a single-use assay specific cartridge for fractionation can enable verification that a particular solvent assembly is compatible with the single-use assay specific cartridge selected by the user. Written codes (e.g. numerical or letter codes), machine readable codes, quick response (QR) codes, bar codes, electronic codes (e.g., RF codes), color codes, physical compatibility (e.g. lock and key fitting that allows only compatible items to connect), or a combination thereof, can be used to identify a solvent assembly as compatible with a single-use assay specific cartridge. Once the user or system has confirmed that the intended solvent assembly is compatible with the cartridge that contains filtered sample in the filtrate reservoir, the user or system introduces solvent into the cartridge through a solvent port, as in box 125. The introduction of solvent progresses the sample-solvent mixture towards the chromatography portion of the cartridge.

As time passes, the user or system supplies, at 130, the cartridge with a mixture of wash solvent and elution solvent in amounts chosen to be compatible with chromatography media in the cartridge, the sample type, and the target analyte so that impurities and the analyte of interest reach the mass spectrometry system at different times. The elution solution with the fractionated sample constituents and standards is passed, at 135, to the mass spectrometric analysis portion of the system to obtain reference data, as well as data regarding the analytes of interest, including the presence or absence of such analytes. Once the mass spectrometric analysis portion of the system has completed data collection, the data from the mass spectrometric analysis portion of the system is reported, at 140, to the user, clinician, or to another system for data analysis. For example, the data can be forwarded to a clinician or a user, such as a caregiver, electronically, through a written report, or both electronically and in a written report. Also, further manipulation of the data may be needed to provide a clinician or other care giver with information that can be used to treat a patient, and another system may perform such data manipulation if the clinician cannot, for example due to time or lack of specific expertise.

Figure 2:
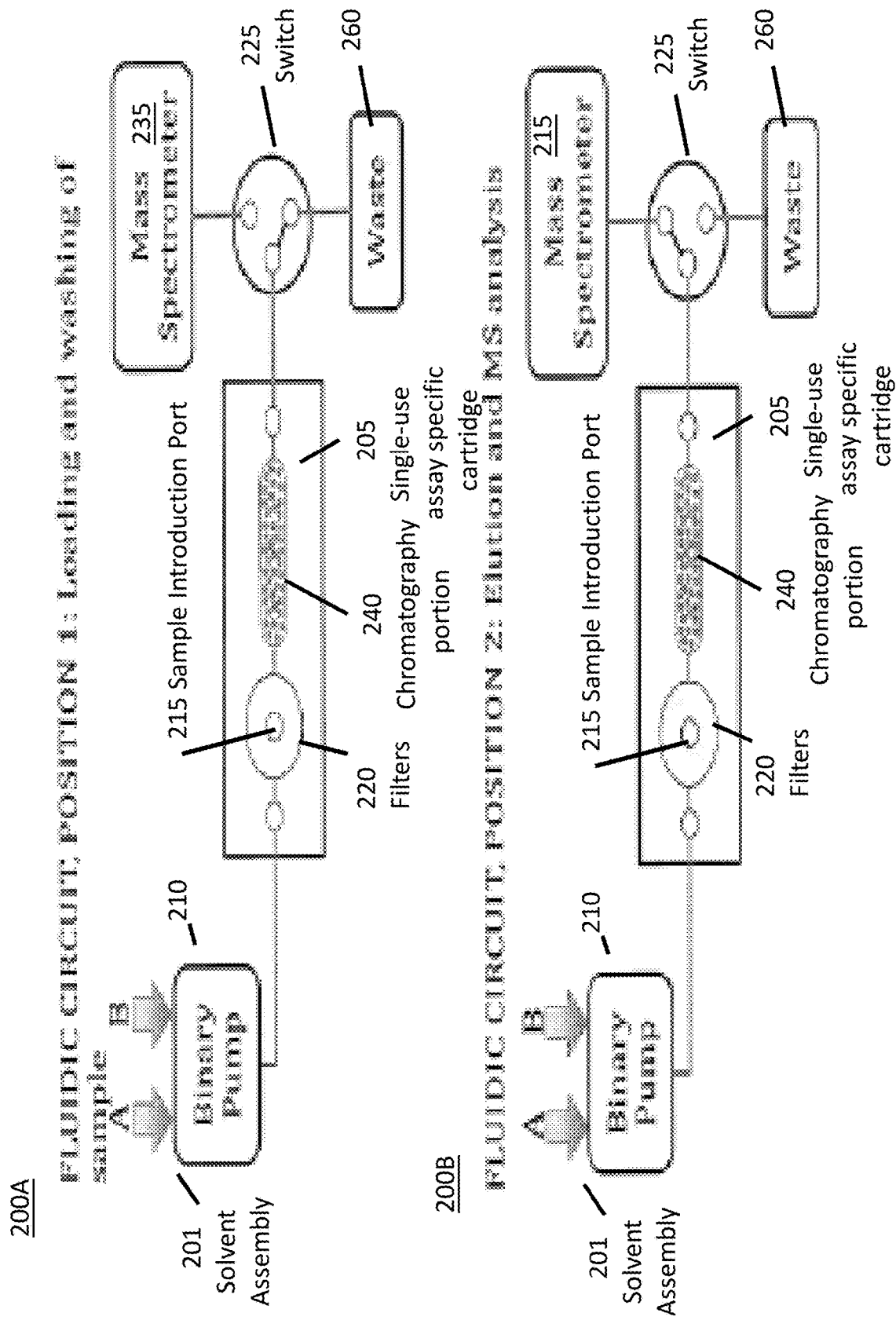
FIG. 2 depicts an exemplary analysis system that includes inlet of two solvents into a single-use, assay specific analysis cartridge.

FIG. 2 shows an example of an embodiment of a system for mass spectrometric analysis that includes a solvent assembly 201, a single-use assay specific cartridge 205, and a switch 225 that allows for toggling between a mass spectrometer 235 and a waste receptacle 260. The top portion 200A shows the system in a configuration suitable for flowing wash solvent through the cartridge 205. In this configuration, the user has inserted the sample through the sample introduction port 215, and the sample has passed through one or more filters 220 into the filtrate reservoir, along with one or more internal standards that are now in solution. The one or more filters 220 remove cells, blood platelets, and/or other precipitates from the sample as it passes into the filtrate reservoir. The solvent assembly 201 has sources for both wash and elution solvents, assuming that they are distinct solvents. During the wash stage 200A, the wash solvent moves the sample and the one or more internal standards towards the chromatography portion 240 of the cartridge 205. The wash solvent flows over the chromatography portion 240 for a predetermined amount of time, and this wash duration is controlled by the user or programmatically/automatically by the system. The switch 225 directs solvent to flow to a waste receptacle 260 at this time, as this wash solution is not suitable for analysis by the mass spectrometer.

The bottom portion of FIG. 2 shows the system in an elution and analysis configuration 200B. In this configuration, the wash solvent has flowed through the filtrate reservoir, taking the sample and standards with it through the chromatography portion 240 of the cartridge 205. The elution solvent is now flowing through the cartridge 205, assisted by a pump 210 in the solvent assembly 201. The switch 225 directs the solution containing elution solvent to the mass spectrometry portion of the system 215. The solution is atomized and the constituents ionized by an ionization source in the MS part of the system. Sufficient fractionation should occur during this process so that salts and buffers do not interfere with the ionization or detection of the target analyte or analytes. Following use, the user or system may dispose of the single-use cartridge. As mentioned above, single use of the cartridge prevents cross contamination of the chromatography media.

The solvent assembly 201 shown in FIG. 2 includes sources for two solvents, A and B, which can be the wash and elution solvents, as well as a pump 210 which can selectively draw from the sources for solvents A and/or B. The sources for solvents A and B are not shown, but they can be reservoirs, such as flasks, beakers, bladders, and the like, which contain volumes of A and B. Alternately, or additionally, the pumps can be syringe-type pumps that directly drive liquid flow from a reservoir. The volumes of A and B can be premixed, commercially available solutions, or the volumes of A and B can be prepared by a skilled user in order to tailor the solvents for use with the single-use cartridge and the biological sample with the target analyte in mind.

The system shown in FIG. 2 can have one or more controllers that accept some user input to control the flow of solvent through the system and the analytical instruments. One or more controllers can control the flow of solvent by controlling mechanisms such as the syringe pump 210 and/or the switch 225. One or more controllers can also control the introduction of liquid sample into the cartridge through the sample introduction port 215. The analysis of fractionated solvent, including any ionization or other preparation that is done prior to mass spectrometric analysis can be controlled by one or more controllers that may receive input from a user. The one or more controllers can include user interfaces, as well as computer processors, memory facilities, data transmission facilities, and the like.

Figure 3:
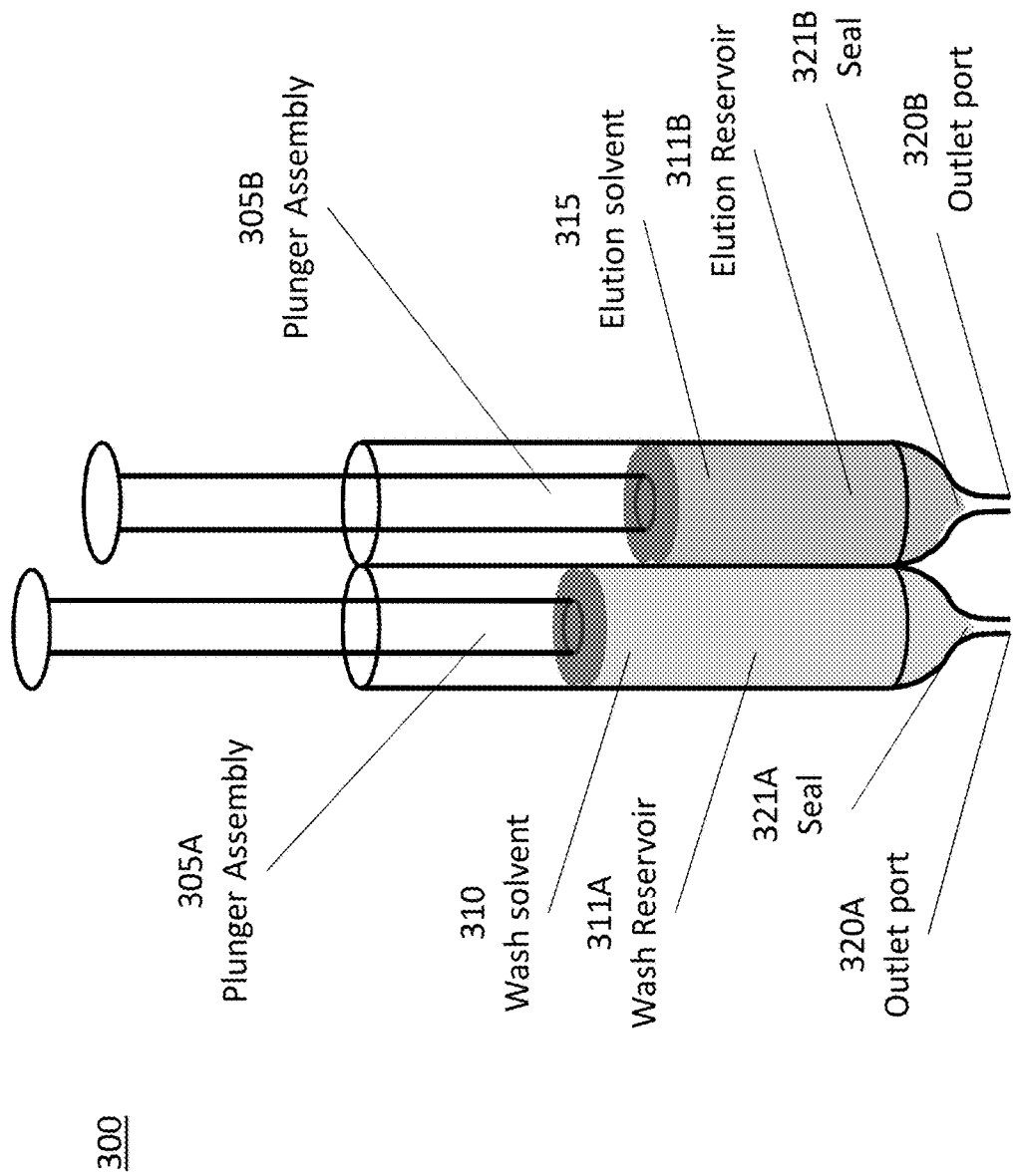
FIG. 3 depicts a dual plunger assembly for wash and elution solvents for use with a single-use, assay specific analysis cartridge.

FIG. 3 shows a solvent assembly 300 that includes two syringes, in accordance with some example embodiments. Each syringe includes a plunger assembly 305A and 305B, an outlet port 320A and 320B, solvent reservoir 311A and 311B, as well as a seal 321A and 321B between the reservoir and the outlet port. The wash solvent 310 is contained within the wash reservoir 311A and the elution solvent 315 is contained within the elution reservoir 311B. Each plunger assembly 305A and 305B can be operated separately by a syringe pump, such as pump 210 in the assembly 201, or by a user by hand, separately to expel the wash solvent 310 and the elution solvent 315.

The wash 310 and elution 315 solvents can mix in a single delivery line or in a separate reservoir that fluidly connects to the single-use cartridge. For example, a first fluid delivery line connected to the wash outlet port 320A and a second line connected to elution outlet port 320B can feed into a "Y" or "T" shaped junction that leads to a third line. In the third line, the wash and elution solvents can mix and then flow into the single-use assay specific cartridge. Alternatively, a first fluid delivery line connected to the wash outlet port 320A and a second line connected to elution outlet port 320B can feed into a mixing reservoir. The wash and elution solvents can combine in the mixing reservoir and then flow toward the sample and chromatography portion of the single-use assay specific cartridge. The mixing reservoir can be external to the cartridge or part of the single-use assay specific cartridge.

Each plunger assembly 305 can be operated separately, as indicated above. Each plunger can be moved by a user's hand or by a motorized mechanism, such as syringe pump 210. A syringe pump 210 can be controlled by an instantaneous user's input, for example, by a push of a button, selection of a value, or typing a command on a controller by a user. Alternatively, or additionally, a program can automatically control a syringe pump 210 to move each plunger assembly 305. Such a program can be selected by the system or user and can move one or both of the plunger assemblies 305 a predetermined amount, in a series of motions, to dispense predetermined amounts of solvent.

The solvent assembly 300 can have two syringes and one or more keys, such as a unique shape at one of, or between, the outlet ports 320. The one or more keys can correspond to one or more features on the single-use cartridge so that the solvent assembly can connect to the single-use cartridge in only one way. Limiting the connection configuration of the solvent assembly and single-use cartridge can avoid errors in solvent use.

For example, the outlet ports 320 can be shaped with a tapered end, similar to Luer-type fittings. In configurations where each of the outlet ports 320 are similar, there can be bridge between the outlet ports 320 that is not straight, that is to say it is curved or angled, so that if the wash solvent plunger 305A is not inserted over the wash solvent inlet port on the cartridge, the solvent assembly 300 will not fit into the cartridge. Alternatively, or additionally, the one or more of the outlet ports 320 can be asymmetrically shaped or have a notched portion, so that the solvent assembly will not fit into the cartridge if not inserted correctly.

The seal of each syringe 321A and 321B can be a material that is compatible with the solvent in each syringe, such that the seal will not degrade over time when exposed to the solvent. The seal of each syringe 321A and 321B can also be a material that is robust enough to endure shipping in various conditions, yet one that pierces without excessive effort when impaled on a pointed surface. Materials that can be used to fabricate the seal include polymers, such as polypropylene, latex, rubber, nitrile, ethylene tetrafluoroethylene (ETFE), polytetrafluoroethylene (PTFE), or any suitable material that is compatible with the selected solvent. The seal 321 can be applied to the entire interior of the reservoir 311 of each syringe or only near, or on, the outlet port 320. The seal 321 can be applied during manufacturing of the syringes, such as just prior to filling the syringe with solvent or after filing the syringe with solvent. Additionally, the syringe walls and each plunger assembly can be made of material compatible with the solvent contained within the syringe. Exemplary syringe and plunger assembly materials can include polypropylene, polyolefins, polycarbonate, Teflon-type fluoroplastic resins (e.g., PTFE), as well as metals, glass, ceramics, and other material able to resist degradation under exposure to the solvent, as well as the operating pressures.

Figure 4:
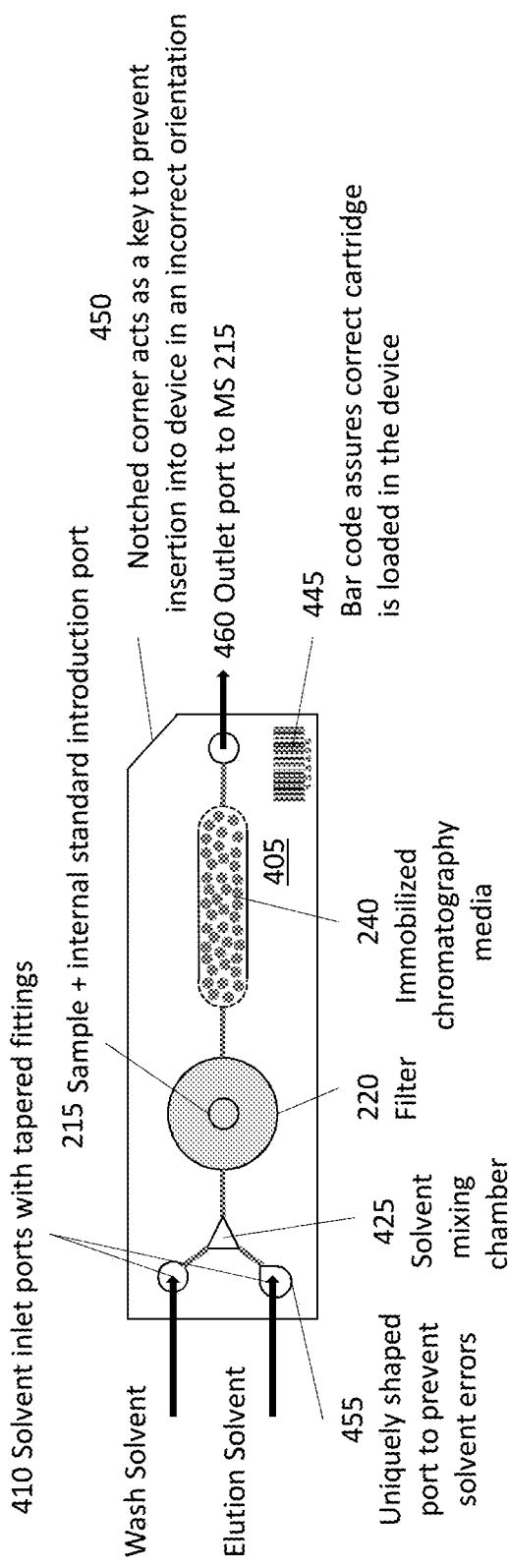
FIG. 4 depicts top and bottom views of an assay specific analysis cartridge showing a solvent mixing chamber.
Figure 4:
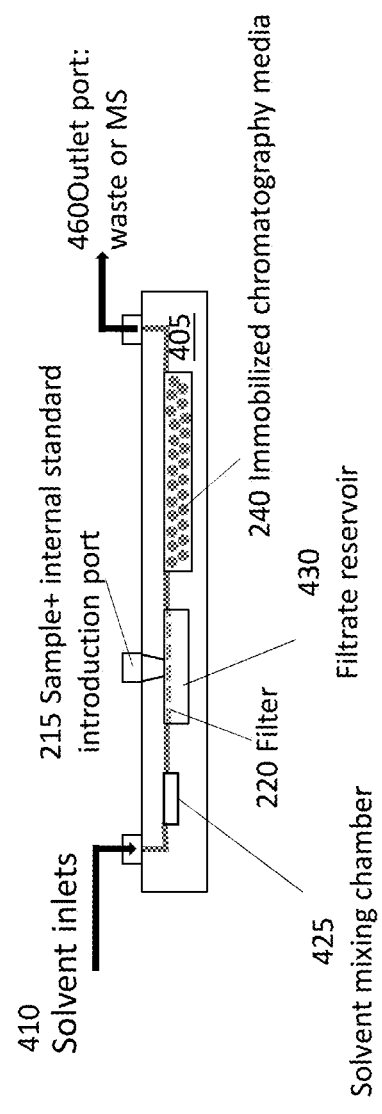

In some example embodiments, the single-use, assay specific cartridge can directly accommodate the solvent assembly 300 shown in FIG. 3. Such a single-use cartridge 405 is shown in FIG. 4. From the top view 400A of the single-use cartridge, solvent inlet ports 410, a solvent mixing chamber 425, a sample introduction port 215, a filter 220, a chromatography portion 240 with immobilized chromatography media, and an outlet port 460 can be seen. Safe-use features such as a bar code 445, a notched corner for directional insertion 450, and/or a key (e.g., a unique shape) 455 associated with at least one of the solvent inlet ports 410 to ensure that the solvents are inserted into the correct port are also shown in FIG. 4. The solvent inlet ports 410 can be specific in terms of the type of solvent, wash or elution, that each accepts. The specificity of the inlet ports 410 can be dictated by one or more keys, such as each port having a different shape 455.

In the top view 400A, it can be seen that the outlet ports 320A and 320B of the solvent assembly 300 connect directly to the solvent inlet ports 410, such that each syringe of the solvent assembly connects to a corresponding inlet port. Wash solvent and elution solvent that enters the cartridge 405 through the solvent inlet ports 410 flow into the solvent mixing chamber 425. In the solvent mixing chamber 425, the wash solvent combines with the elution solvent. The incoming solvent is forced into the solvent mixing chamber 425 by a mechanism that actuates the plunger assemblies 305 of the solvent assembly 300, such as a syringe pump 210 or a mechanical actuator, like a stepper motor. Eventually, the mixed solvent flows into the filtrate reservoir 430. Before the mixed solvent flow into the reservoir 430, the filtrate reservoir 430 can contain internal standards and filtered sample that is sample without precipitates such as cells. The filtered sample combined with the mixed solvent flows into the chromatography portion 240 of the cartridge, flowing over the immobilized chromatography media. The biological sample is fractionated by the chromatography media in the chromatography portion 240 and passes through the outlet port 460 either to a waste receptacle 260 or to the mass spectrometric analysis portion of the system 235. In some example embodiments, a switch 225 directs the flow of fractionated solvent, such as by selectively opening valves or by repositioning conduits between the outlet and either the waste receptacle 260 or the mass spectrometry system 215.

The side view of the cartridge 400B, allows for a better view of the relative location and size of the solvent inlets 410, the mixing chamber 324, the filtrate reservoir 430, as well as the ports. The solvent inlets ports 410, sample introduction port 215, and the outlet port 460 are shown as situated on the top portion of the cartridge 405, connected to chambers and reservoirs via fluid conduits. The solvent inlets 410 are at a first end of the cartridge 405, opposite the end of the cartridge 405 with the outlet port 460. The sample and internal standard introduction port 215 is located in the central portion of the cartridge 405, directly over the filtrate reservoir 430.

In some example embodiments, the internal standards used with the single-use cartridge 405 are pre-loaded into the cartridge 405, such as within or on the filter 220, or within the filtrate reservoir 430. Alternatively, the user or system can introduce the internal standards via the sample introduction port 215. In some embodiments, the single-use assay specific cartridge 405 can operate with both pre-loaded internal standards, as well as with internal standards materials introduced through the sample introduction port 215. Such flexibility with respect to the internal standard can increase the number of assays a single-use cartridge can be used for.

Codes on the cartridge and solvent assemblies can be included to ensure compatibility between the single-use, assay specific cartridge and the solvent assemblies, including the solvent within the syringes of the solvent assemblies. Codes can include machine readable codes, bar codes, RFID (radio frequency) codes, quick recognition (QR) codes, suitable visual codes, suitable electromagnetic codes, and the like. The system can read the code on the cartridge prior to introduction of the sample, after introduction of the sample, before piercing the seals on the solvent assemblies, or any combination thereof. The code on the solvent assembly can be read by the system before piercing the seals on the assembly, before reading the code on the cartridge, or after reading the code on the cartridge. The system can alert the user to an incompatibility between the cartridge and solvent assembly with a visual alarm, an audio alarm, or both. The system can also prevent an analysis from progressing when incompatible solvents are detected in the form of an incompatible solvent assembly.

FIG. 4 shows a bar code 445 located on one corner of the top portion of the single-use cartridge 405, adjacent the outlet port 460. The notched corner 450 that acts as a key to prevent improper insertion of the cartridge 405 into a system is shown opposite the bar code 445, adjacent the outlet port 460. The notched corner 450 is shown as continuing through the thickness of the cartridge 405, but in some example embodiments, a notched corner in a single-use cartridge can pass only partially through the thickness of the cartridge. Additionally, or alternatively, the bar code 445, or other codes that indicate which type of assay the cartridge 405 is compatible with, can be located on other portions of the cartridge. The other portions of the cartridge can include any portion that can be read by a user or the system, such as on a lateral side of the cartridge, on another corner of the top portion of the cartridge, on the back of the cartridge on the side opposed to all of the inlet ports, or any combination thereof.

Figure 5:
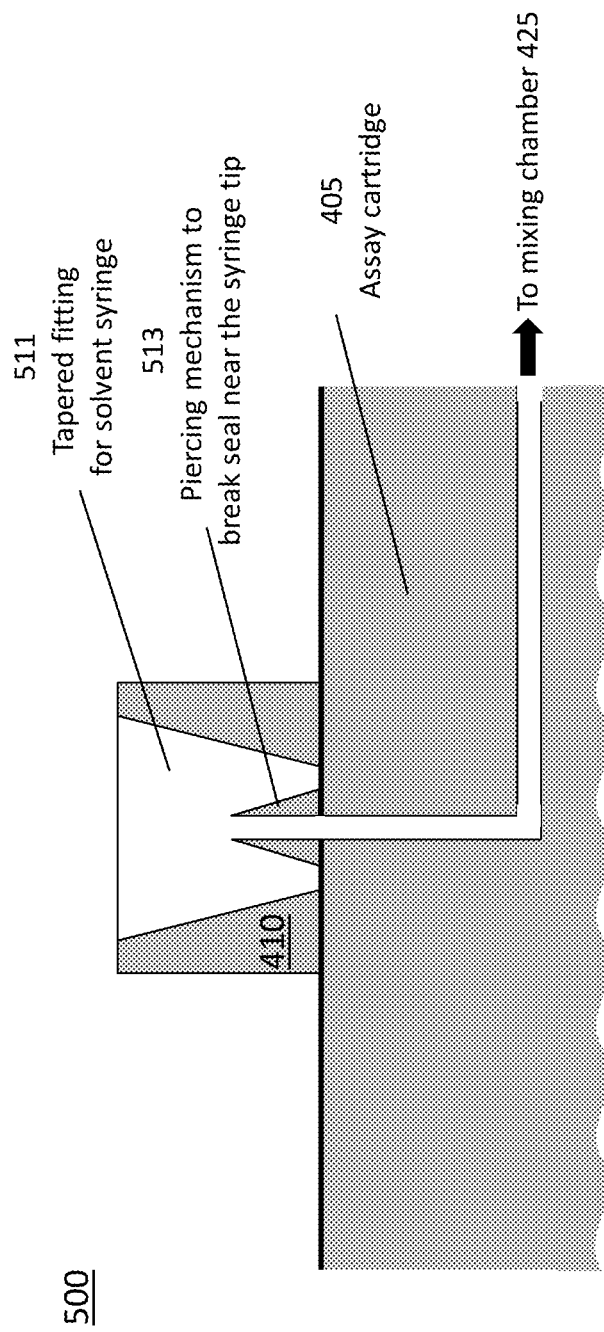
FIG. 5 depicts a detailed view of a tapered inlet port and a fluidic connection to the mixing chamber shown in FIG. 4.

FIG. 5 shows cross-section 500 of a portion of the single-use assay specific cartridge 405 that cuts through one of the solvent inlets 410. The solvent inlet 410 shown includes a tapered fitting 511 that matches the shape of the outlet of one of the solvent syringes, as well as a piercing mechanism 513 that is configured to break the seal on the syringe near the syringe tip or outlet. The piercing mechanism 513 can be sharp, pointy, with at least one opening to a fluid conduit that allows solvent to flow toward the solvent mixing chamber 425 in the single-use assay specific cartridge 405. In FIG. 5, the piercing mechanism 513 is shown as triangular components that protrude up from the surface of the cartridge 405, about the center of the solvent inlet 410. The piercing mechanism 513 can include annular shapes, discrete spikes or columns, as well as annular shapes with perforations through their walls that lead to a conduit that allows solvent to flow toward the solvent mixing chamber 425.

Figure 6:
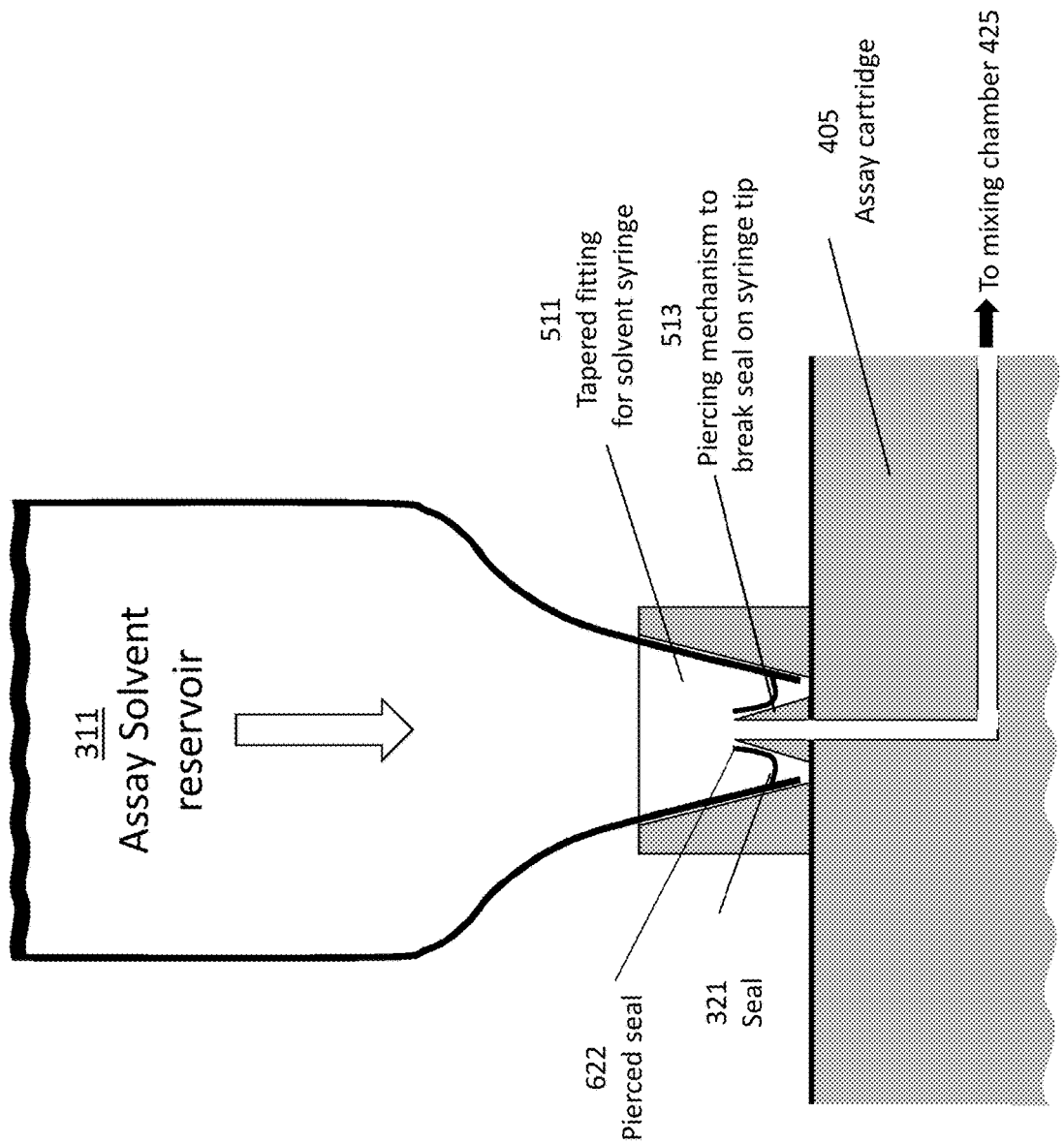
FIG. 6 depicts a solvent inlet port with a docked solvent syringe in an exemplary cartridge.

FIG. 6 shows a syringe of the solvent assembly of FIG. 3 interfacing with a solvent inlet port 410, as shown in FIG. 5. The arrow within the assay solvent reservoir shows that piercing the seal 321 allows for solvent flow from the syringe into the fluid conduit in the single-use assay specific cartridge 405 towards the solvent mixing chamber 425. The seal 321 that separates the solvent within the syringe from the outermost portion of the outlet port 320 is pierced by the piercing mechanism 513 when the syringe is fitted with the outlet port 320 of the syringe in the tapered fitting 511, resulting in a pierced seal 622. The tight fit between the outlet port 320 of the syringe and the tapered fitting 511 allows solvent to flow only into the cartridge 405. The piercing mechanism can break the seal 321 when the system is sealed or closed, such as during the start of operation of the analysis system.

Figure 7:
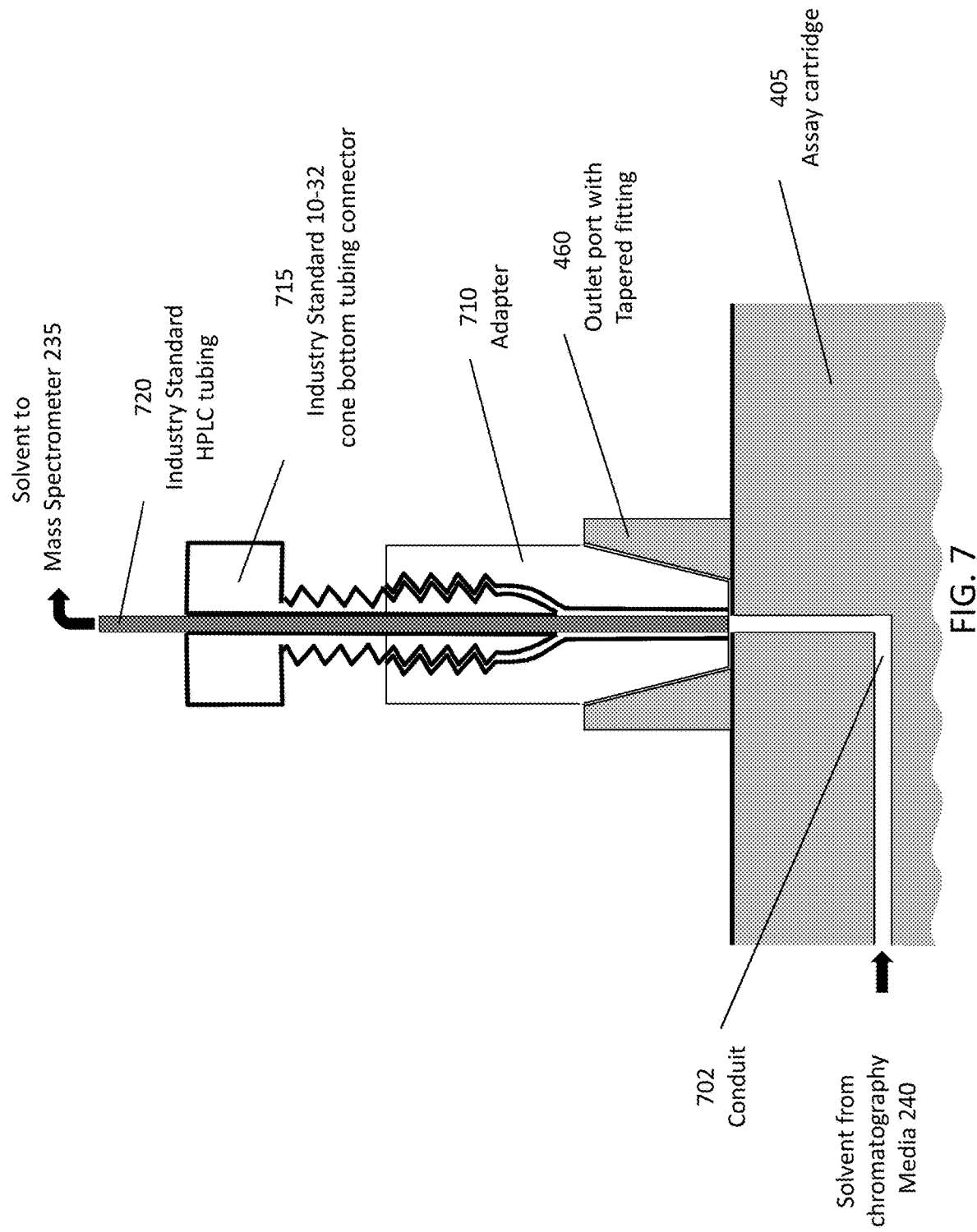
FIG. 7 depicts an exemplary cartridge outlet port showing connection to standard high-pressure liquid chromatography (HPLC) tubing and an interface to a mass spectrometer.

FIG. 7 shows an exemplary flow of solvent out of the single-use cartridge 405, through a conduit 702, from the chromatography media 240 towards the mass spectrometry portion of the system 235. The outlet port of the cartridge 460 can have a tapered fitting that receives an adapter 710 that connects to standardized tubing 715 that accommodates industry standard HPLC tubing 720. The high-pressure liquid chromatography (HPLC) industry standard tubing 720 can connect to the conduit 702 from the chromatography media and convey solvent with analytes and internal standards to the mass spectrometer portion of the system. The tapered fitting at the outlet port 460 can be a Luer-type fitting in which needs no piercing mechanism. In some embodiments, leak-tight fluidic connections between the tapered fitting at the outlet port 460 and the adapter 710 can be established when the system is sealed, that is closed-up, prior to starting analysis.

In some example embodiments, a single-use assay specific cartridge can be supplied with a solvent assembly in an assay kit, such as in a sealed pouch. The kit can be designed for use with a specific instrument that can control the addition of a biological sample and the solvents. The instrument can also control atomization and ionization of the sample, and eventual analysis using a mass spectrometer.

In an implementation, a user inserts the cartridge in the orientation that is accepted by the instrument. That orientation is dictated by the notch in the cartridge shown in FIG. 4. Similarly, the solvent assembly is inserted into the instrument in the orientation dictated by a key feature, as described above. Closing a lid on the instrument triggers the system to verify the compatibility of the cartridge and the solvent assembly, such as by verifying that the codes match, as well as fluidly joining the solvent assembly to the single-use cartridge once compatibility is confirmed.

The user adds at least a minimum required amount of biological sample, such as blood, through an opening in a lid of the instrument that allows access to the sample inlet port on the cartridge. The biological sample solubilizes the one or more dried internal standards within the cartridge. The sample moves through the filters so that cells, platelets, lipids, and other precipitates are removed from the sample, and the precipitate-free sample is collected in the filtrate reservoir. The filtrate reservoir has a metered volume, such as 3 microliters, that is a known volume. The user or system fills the filtrated reservoir to the known volume with biological sample before fractionation begins so that concentrations and amounts of analyte can be calculated by the system. The user or instrument then blocks the sample inlet port, and the instrument causes the solvents to flow through the cartridge, as described above, fractionating the constituents in the sample so that reliable results can be obtained from the mass spectrometer.

Though the system has been described in use with one single-use assay specific cartridge, the system may be configured to accept multiple cartridges. For example, multiple single-use assay specific cartridges may be loaded into a system, each cartridge testing for different analytes, so that biological samples from a single patient can be tested serially, in an automated fashion. Similarly, methods that describe using a system with only one single-use assay specific cartridge can be applied to systems that can accept and utilize multiple assay specific cartridges at once.

Without in any way effecting the scope of the claims, a technical effect of the systems, methods, apparatus, and kits, described herein includes time and labor savings, elimination of potential errors, streamlined logistics and inventory management, improved safety, elimination of solvent quality control and quality assurance, and/or elimination of solvent waste.

The systems, methods, apparatus, and kits, described herein can be used in many situations, including situations in which a patient arrives in an emergency room and is suspected to have, or exhibits, the following conditions: acidosis, intentional overdose, uncontrolled seizures or convulsions, being comatose or unresponsiveness, and cardiovascular arrhythmia and/or hypotension, usually seen in geriatric patients. In some such instances, the analysis system does not need to be absolutely accurate in terms of the amount of analyte present in a sample, rather only the detection of a toxic or overdose level of an analyte needs to be determined. The following are exemplary situations in which systems, methods, apparatus, and kits, described herein can find use.

Metabolic Acidosis: When a patient presents with acidosis (i.e.: low blood pH) there are several possible causes. Ingestion of a toxic alcohol such as methanol or ethylene glycol leads to acidosis, but there could be other causes not related to a toxic exposure such as starvation, metabolic disorders, diabetes, asthma, strenuous exercise, and the like. There are few tools at the disposal of the physician (e.g., pH measurements, osmololal gap measurement) to make a diagnosis as to the cause of acidosis or to direct the course of treatment.

Toxic alcohol induced acidosis presents similarly to metabolic acidosis, but these conditions have very different treatments. Toxic alcohol exposure requires fomepizole treatment at low concentrations (e.g., below 50 mg/mL) and hemodialysis at higher concentration (e.g., above 50 mg/mL), while metabolic acidosis requires treating the underlying condition. As toxic alcohol poisoning can cause permanent damage (e.g., optic nerve and kidney toxicity) and potentially be fatal if not treated promptly, patients with acidosis and suspected exposure are often dialyzed as precautionary measure. The current assay for toxic alcohols requires specialized instrumentation (e.g., gas chromatography (GC) or GCMS) and trained staff that are not widely available.

The ideal assay panel would measure the concentration of toxic alcohols and their metabolites along with several markers of metabolic activity in the patient. Lactate and pyruvate levels are key markers of the energy state in a healthy cell. If there is a metabolic disorder, the lactate/pyruvate levels become altered, so these levels can provide an important diagnostic clue to a physician or other caregiver.

Specific assays of interest in the toxic alcohol panel can include methanol, isopropanol, ethylene glycol and their metabolites formic acid, acetone, and glycolic acid, respectively. Lactate and pyruvate are of interest to help in diagnosing causes of acidosis or ketosis that may be unrelated to exposure to toxic alcohols. One kit could test a patient's blood or urine for these alcohols using the systems and methods described herein, as well as possibly indicating the levels, or relative levels, of lactate and pyruvate.

Intentional overdose (OD) panel: The archetypal OD patient is a 16-25 year old female who intentionally overdoses on prescription medication. Often the drug, typically an antidepressant or anxiety medication, that was ingested by the patient is known to the emergency room physician. Wellbutrin and Celexa in particular need to be monitored very closely due to possibility of late onset seizures, sometimes days after the initial exposure. Furthermore, the current standard of care is to test each and every intentional overdose patient for Tylenol (acetaminophen) and Aspirin (salicylic acid) given the ability of these common drugs to cause liver damage and that can result in complications for an OD patient. A kit could include solvents and a cartridge including chromatography media to fractionate samples so that acetaminophen, salicylic acid, as well as anti-depressants at toxic levels could be detected. This could be a single kit or two or more kits.

Uncontrolled convulsions or seizures: When a patient is admitted to the ER with uncontrolled seizures or convulsions there may be multiple causes including an underlying seizure disorder like epilepsy or a completely unrelated non-physiological cause such as an overdose of a drug such as cocaine or methamphetamines that cause convulsions. The seizure panel would test the patient for commonly prescribed anti-convulsant drugs like Lamotrigine, carbamazepine and Keppra to determine if the patient has a sub-therapeutic systemic dose due to missed medications or a change in the presentation of the disease. The panel would also monitor compounds known to cause convulsions or seizures such as amphetamines, cocaine, buproprion (wellbutrin), citalopram (celexa) and possibly others. This panel could consist of two assay kits—the first designed to prepare samples for detecting medications to treat seizure disorders and the second designed to prepare samples for detecting likely toxin induced seizure agents.

While the panel would not be capable of looking at every drug known to cause or prevent seizures, a set of assay kits that cover the top 4-5 agents would help physicians to diagnose a large percentage of patients. The treatment for a patient who has missed several doses of his seizure medication is very different from one who has overdosed on cocaine, so knowing what has been ingested by a patient is crucial.

Coma Panel: Another common ER patient is an unresponsive or comatose patient. In this case the physician is interested in determining whether or not the patient has ingested a large amount of sedatives, including prescription and illegal opiates, benzodiazepines, and heroin. Not every possible drug or sedative can be measured in a single panel, but assay kits can focus on the most commonly observed agents. Even a negative result for the agents being assayed is important, as it will help the physician rule out the most obvious and common causes and allow him or her to shift attention to other possible causes for the condition of the patient.

Cardiovascular Panel: The archetypal patient is an elderly person with arrhythmia, bradycardia, and/or hypotension. Many of these patients are on multiple medications and it is common that dosing of one or more of the drugs is incorrect, either due to lack of patient compliance or a change in the underlying disease. An assay kit could be designed to allow the systems described herein to detect beta-blockers, calcium channel inhibitors, and anti-arrhythmia drugs, specifically propafenone, clonidine, guanfacine, and the like. However, over time, the list of particular drugs can change as pharmaceutical markets evolve. A rapid blood test can help the physician diagnose the potential issue with the patient, which is often due to an accidental overdose or missed doses (i.e.: an underdose) of an already prescribed medication.

The subject matter described herein may be embodied in systems, apparatus, methods, and/or articles depending on the desired configuration. For example, the scanning system (or one or more components therein) and/or the processes described herein can be implemented using one or more of the following: a processor executing program code, an application-specific integrated circuit (ASIC), a digital signal processor (DSP), an embedded processor, a field programmable gate array (FPGA), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the phrase "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. In various example implementations, the methods (or processes) can be accomplished on mobile station/mobile device side or on the server side or in any shared way between server and user equipment/mobile device with actions being performed on both sides. The phrases "based on" and "based on at least" are used interchangeably herein. Other implementations may be within the scope of the following claims.

What is claimed:

1. A cartridge for preparing an analyte of interest in a biological sample for mass spectrometry analysis, the cartridge comprising:
   a housing;
   a solvent inlet in the housing comprising configured to introduce solvents into the cartridge, at least a portion of the solvent inlet has an asymmetrical shape;
   a sample introduction port in the housing fluidly connected to the solvent inlet and configured to receive a biological sample comprising an analyte of interest;
   a chromatography region in the housing fluidly connected to the sample introduction port; and
   an outlet from the housing fluidly connected to the chromatography region,
   wherein the solvent inlet of the cartridge is configured to fluidly connect with an outlet of a solvent assembly for mass spectrometry analysis, and
   wherein the asymmetrical shape of the at least a portion of the solvent inlet is configured to fit together with the outlet of the solvent assembly in a specific orientation to provide an indication that the cartridge is compatible with the solvent assembly for performing an assay to determine the concentration of the analyte of interest.

2. The cartridge of claim 1, further comprising immobilized chromatography media in the chromatography region of the cartridge.

3. The cartridge of claim 2, wherein the immobilized chromatography media corresponds to the assay.

4. The cartridge of claim 1, further comprising one or more filters in the cartridge, wherein the one or more filters are configured to remove precipitates and/or insoluble material from the biological sample and yield a filtered biological sample.

5. The cartridge of claim 4, further comprising a filtrate reservoir in the cartridge, wherein the filtrate reservoir has a metered volume and is configured to contain the filtered biological sample.

6. The cartridge of claim 1, wherein the assay comprises at least one of a metabolic acidosis assay, an intentional overdose assay, an uncontrolled convulsions or seizures assay, a coma assay, or a cardiovascular assay.

7. The cartridge of claim 6, wherein the assay comprises one or more test panels.

8. The cartridge of claim 1, further comprising one or more codes coupled to the housing indicating the compatibility of the solvent assembly with the cartridge to perform the assay to determine the presence of the analyte of interest.

9. The cartridge of claim 8, wherein the one or more codes comprise color coding, written codes, machine readable codes, electrical signaling codes, or any combination thereof.

10. The cartridge of claim 9, wherein the written codes comprise alpha-numeric codes, symbols, or a combination of both.

11. The cartridge of claim 9, wherein the machine readable codes comprise symbols, quick response (QR) codes, barcodes, or any combination thereof.

12. The cartridge of claim 1, wherein the cartridge is disposable and configured for single-use.

13. The cartridge of claim 1, wherein the sample introduction port comprises a plurality of internal standards in dried form.

14. The cartridge of claim 13, wherein the plurality of internal standards comprises at least one of a plurality of isotopes of the analyte of interest or a plurality of derivatized samples of the analyte of interest added to the biological sample in a single spectral measurement.

15. The cartridge of claim 13, wherein the plurality of internal standards correspond to the assay.

16. The cartridge of claim 1, wherein the housing of the cartridge includes a plurality of corners, wherein one of the plurality of corners is a notched corner.

17. The cartridge of claim 16, wherein the notched corner passes partially through a thickness of the housing.

* * * * *